US009138591B2

(12) United States Patent
Abbenhouse et al.

(10) Patent No.: US 9,138,591 B2
(45) Date of Patent: Sep. 22, 2015

(54) MEDICAL DEVICE WITH LANGUAGE LOCALIZATION

(75) Inventors: Martin Abbenhouse, Kirkland, WA (US); David R. Christie, Woodinville, WA (US); Daniel Conan Perreault, Everett, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 237 days.

(21) Appl. No.: 13/552,549

(22) Filed: Jul. 18, 2012

(65) Prior Publication Data

US 2014/0025128 A1      Jan. 23, 2014

(51) Int. Cl.
  *A61N 1/39* (2006.01)
  *G09B 23/28* (2006.01)
(52) U.S. Cl.
  CPC ............ *A61N 1/3993* (2013.01); *G09B 23/288* (2013.01)
(58) Field of Classification Search
  CPC ................................ A61N 1/39; A61N 1/3993
  USPC ............................................................. 607/5
  See application file for complete search history.

(56) References Cited

U.S. PATENT DOCUMENTS

| 2004/0049234 | A1* | 3/2004 | Morgan et al. ................... 607/5 |
| 2006/0069326 | A1* | 3/2006 | Heath .............................. 601/41 |
| 2008/0097533 | A1* | 4/2008 | Halsne ............................. 607/5 |
| 2012/0112903 | A1* | 5/2012 | Kaib et al. ................ 340/539.12 |
| 2013/0012151 | A1* | 1/2013 | Hankins ..................... 455/404.1 |

FOREIGN PATENT DOCUMENTS

| WO | 2005082454 A1 | 9/2005 |
| WO | 2006016288 A1 | 2/2006 |

\* cited by examiner

*Primary Examiner* — Carl H Layno
*Assistant Examiner* — Jennifer Ghand
(74) *Attorney, Agent, or Firm* — Marger Johnson

(57) ABSTRACT

An external medical device can include a housing, an energy storage module within the housing for storing an electrical charge, and a defibrillation port for guiding via electrodes the stored electrical charge to a person. The device can also include a user interface to deliver prompts to a user during a defibrillation session and a language detector in the housing to determine a vicinity language. The prompts can be in a language that is selected based on the determined vicinity language.

28 Claims, 10 Drawing Sheets

EXTERNAL DEFIBRILLATOR
ACCORDING TO EMBODIMENTS

FIG. 1  *DEFIBRILLATION SCENE*

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

FIG. 2  *TWO MAIN TYPES OF EXTERNAL DEFIBRILLATORS*

FIG. 3

*COMPONENTS OF EXTERNAL DEFIBRILLATOR*

FIG. 4

EXTERNAL DEFIBRILLATOR
ACCORDING TO EMBODIMENTS

FIG. 5A  EXTERNAL DEFIBRILLATOR IN PUBLIC ENVIRONMENT

FIG. 5B  EXTERNAL DEFIBRILLATOR IN PUBLIC ENVIRONMENT

FIG. 5C

*EXTERNAL DEFIBRILLATOR IN PUBLIC ENVIRONMENT*

FIG. 5D

*EXTERNAL DEFIBRILLATOR IN PUBLIC ENVIRONMENT*

*EXTERNAL DEFIBRILLATOR IN PUBLIC ENVIRONMENT*

FIG. 7　　METHODS

FIG. 8   *METHODS*

FIG. 9 METHODS

MEDICAL DEVICE WITH LANGUAGE LOCALIZATION

FIELD

This invention generally relates to medical devices such as external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

BRIEF SUMMARY

The present description gives instances of devices, systems, software and methods, the use of which may help overcome problems and limitations of the prior art.

In certain embodiments, an external medical device may include a housing, an energy storage module within the housing for storing an electrical charge, and a defibrillation port for guiding via electrodes the stored electrical charge to a person. The device may also include a user interface to deliver prompts to a user during a defibrillation session and a language detector in the housing to determine a vicinity language. The prompts delivered by the user interface to the user during the defibrillation session can be in a language that is selected based on the determined vicinity language. The prompts may include visible prompts, audible prompts, or a combination thereof.

An advantage over the prior art is that an external medical device in accordance with the disclosed technology can deliver prompts to a user in a language that is understood by the user. Should a user need to initiate or otherwise assist with a defibrillation session at a location where multiple languages are spoken, such as an international airport, for example, the external medical device can deliver prompts to the user in a language that is selected based on a determined vicinity language and thus likely to be understood by the user.

These and other features and advantages of this description will become more readily apparent from the following Detailed Description, which proceeds with reference to the drawings, in which:

BRIEF DESCRIPTION OF THE DRAWINGS

FIG. 2 is a table listing two main types of the external defibrillator shown in FIG. 1, and who they might be used by.

DETAILED DESCRIPTION

As has been mentioned, the present description is about medical devices, methods of operating such medical devices, and a programmed processor to control such medical devices for controlling enabling features of the medical device based on language localization.

Embodiments are now described in more detail.

Figure 1:
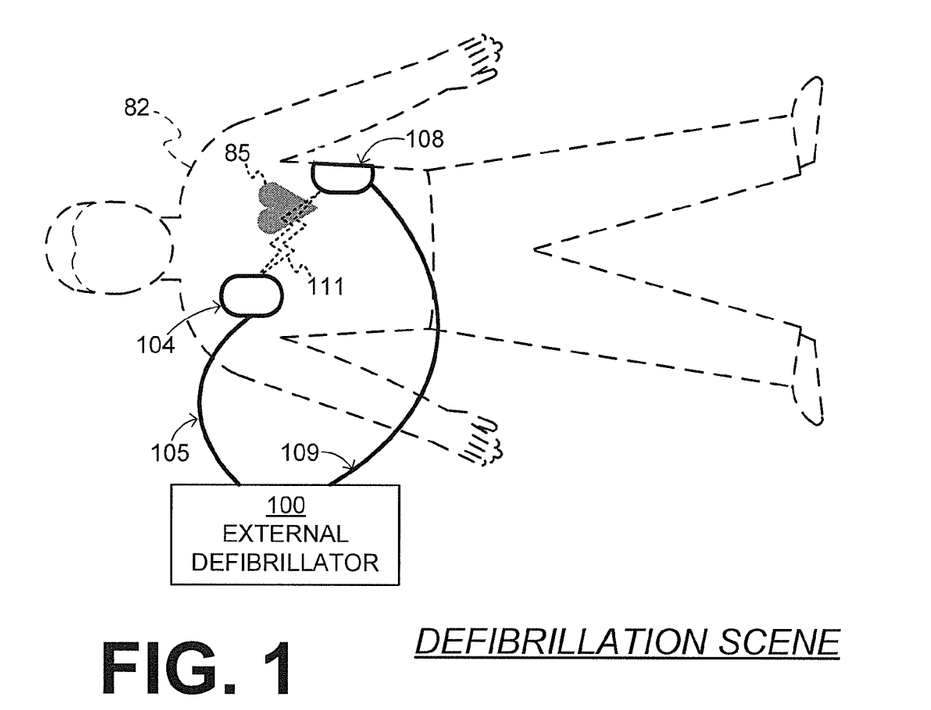
FIG. 1 is a diagram of a scene where an external defibrillator is used to save the life of a person according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

Figure 2:
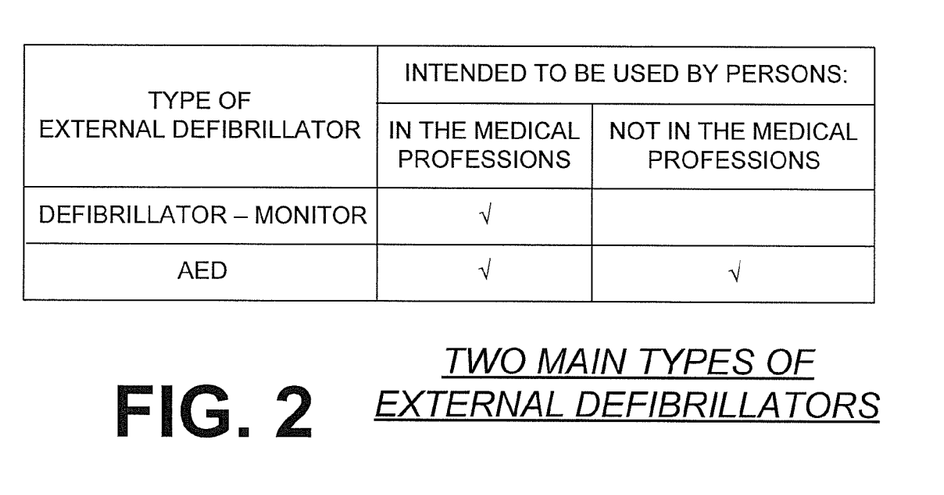

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

Figure 3:
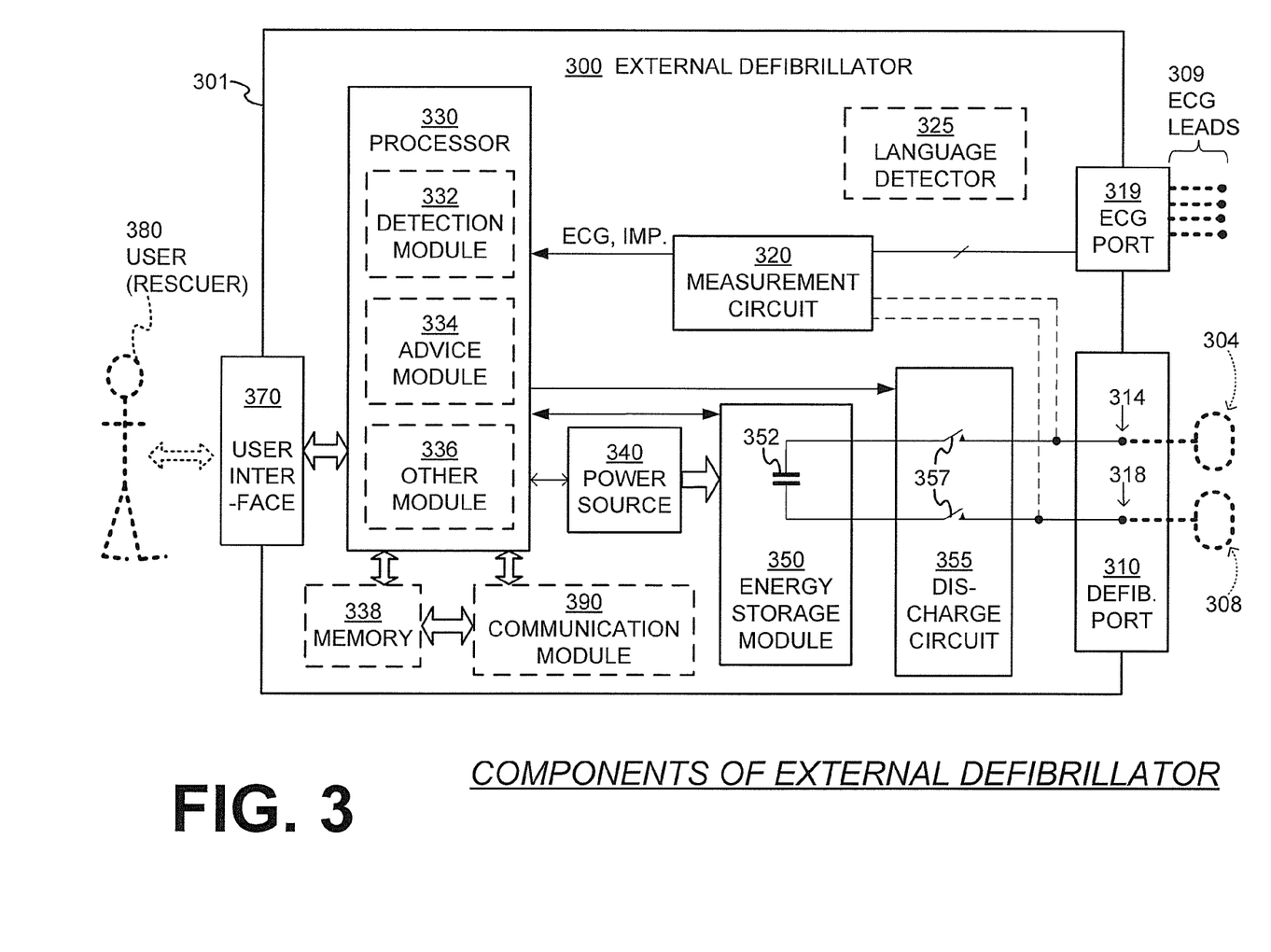
FIG. 3 is a functional block diagram showing components of an external defibrillator, such as the one shown in FIG. 1, which is made according to embodiments.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and a language detector 325 structured to determine a vicinity language.

The language detector 325 may determine the vicinity language based on one or more inputs received by the defibrillator 300. Alternatively or in addition the language detector 325, the defibrillator 300 may include a language selector structured to select a language for the defibrillator 300 to use when delivering prompts to a user. The language used by the defibrillator 300 may be the vicinity language or it may be a different language than the vicinity language. In these embodiments, the different language may be selected based at least in part on the determined vicinity language.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visual or by sound, so that the user can administer CPR. Examples are taught in U.S. Pat. No. 6,334,070 and No. 6,356,785.

Figure 4:
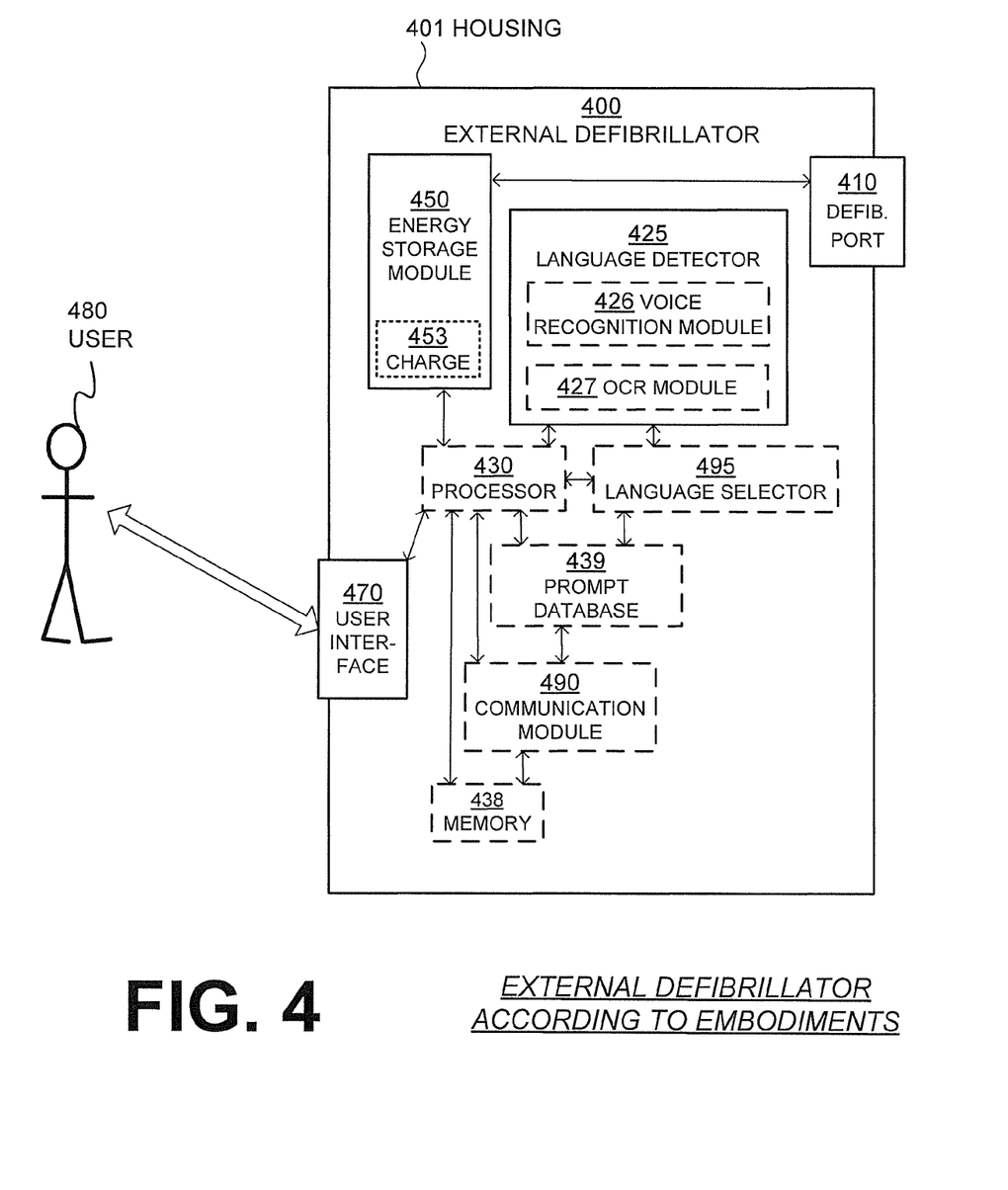
FIG. 4 is a functional block diagram showing components of another external defibrillator, such as the one shown in FIG. 1, which is made according to certain embodiments.

FIG. 4 is a functional block diagram showing components of another external defibrillator 400, such as the one shown in FIG. 1, which is made according to certain embodiments. Defibrillator 400 includes a housing 401, an energy storage module 450 within the housing 401 for storing an electrical charge 453, a defibrillation port 410 for guiding via electrodes the stored electrical charge 453 to a person, a processor 430, a memory 438, and a communication module 490. Defibrillator 400 also includes a user interface 470 structured to deliver prompts to a user 480 during a defibrillation session. The prompts may include one or more audible prompts, one or more visible prompts, or a combination of one or more audible prompts and one or more visible prompts.

Defibrillator 400 further includes a language detector 425 in the housing 401 structured to determine a vicinity language. The prompts delivered by the user interface 470 to the user 480 during the defibrillation session are in a language that is selected based on the determined vicinity language. In certain embodiments, the vicinity language is a language spoken by the user 480 when using the device 400. Language detector 425 optionally includes a voice recognition module 426, an optical character recognition (OCR) module 427, or both a voice recognition module 426 and an OCR module 427. In certain embodiments, the processor 430 includes the language detector 425.

Defibrillator 400 optionally includes a language selector 495 in the housing 401 structured to select the language in which the prompts are delivered by the user interface 470 to the user 480 during the defibrillation session. In certain embodiments, the language selector 495 selects the vicinity language as the language in which the prompts are delivered by the user interface 470 to the user 480 during the defibrillation session. In other embodiments, the language selector 495 selects a language other than the vicinity language as the language in which the prompts are delivered by the user interface 470 to the user 480 during the defibrillation session. User interface 470 may be structured to prompt the user 480 to provide a confirmation of the vicinity language.

In certain embodiments, the user interface 470 is structured to deliver the prompts to the user 480 in an initial language. Alternatively, the user interface 470 may be structured to deliver the prompts to the user 480 in a default language. User interface 470 may be structured to not stop delivering the prompts to the user 480 in the selected language after a specified period of time has passed during the defibrillation session.

In certain embodiments, the user interface 470 delivers the prompts to the user 480 in the vicinity language. In these embodiments, the user interface 470 may be further structured to stop delivering the prompts in the vicinity language responsive to an indication to change languages. User interface 470 may be structured to receive the indication to change languages from the user 480. The indication to change languages may be based on a determination that the vicinity language is incorrect. Alternatively, the indication to change languages may be based on a determination that the user 480 is speaking a language that is different from the vicinity language. In certain embodiments, the user interface 470 is further structured to revert back to delivering the prompts to the user 480 in an initial language. In other embodiments, the user interface 470 is further structured to begin delivering the prompts to the user 480 in a default language.

User interface 470 may be structured to receive a "set language" command from the user 480. In these embodiments, the language detector 425 may be structured to determine the vicinity language responsive to the user interface 470 receiving the "set language" command from the user 480. The language selector 425 may be structured to select, responsive to the user interface 470 receiving the "set language" command from the user 480, the language in which the prompts are to be delivered by the user interface 470 to the user 480 during the defibrillation session.

In certain embodiments, the user interface 470 is further structured to prompt the user 480 to provide an indication of the vicinity language. In these embodiments, the language detector 425 may be structured to determine the vicinity language based on the indication provided by the user 480. Language detector 425 may be further structured to evaluate whether the indication provided by the user 480 meets a threshold confidence level. User interface 470 may deliver the prompts to the user 480 in the selected language responsive to an evaluation that the indication meets the threshold confidence level. The indication provided by the user 480 may include verbal feedback, visual cues, or verbal feedback and visual cues. Defibrillator 400 may optionally include a camera unit in the housing 401 structured to capture the visual cues.

Language detector 425 may be optionally structured to monitor ambient sounds, such as a radio station broadcast or a public announcement (PA) from a PA system, for example. In these embodiments, the selected language may be based at least in part on the ambient sounds.

In certain embodiments, the language selector 495 is structured to determine whether the selected language is supported by the device 400. Responsive to a determination that the selected language is not supported by the defibrillator 400, the user interface 470 may be structured to use an initial language, e.g., a default language, when delivering the prompts to the user 480.

Defibrillator 400 optionally includes a database 439 structured to store the prompts in each of a plurality of supported languages. In these embodiments, the language selector 495 may be structured to determine whether the selected language is one of the plurality of supported languages. The database 439 may be within the housing 401. Alternatively or in addition thereto, the database 439 may be at a location that is remote from the defibrillator 400. In embodiments where the database 439 is located remote from the device defibrillator, the communication module 490 within the housing 401 may establish a wireless connection to provide access to the database 439.

In certain embodiments, the user interface 470 is structured to present at least one language option to the user 480. User interface 470 may present the at least one language option to the user 480 visibly, audibly, or both visibly and audibly. In certain embodiments, the user interface 470 is structured to present two or more language options to the user. In these embodiments, the two or more language options may be similar to each other.

In certain embodiments, a record may be created from one of diagnosing and treating the person. In these embodiments, a code may be entered in the record that denotes the detected vicinity language. A time may be further determined, and a code may be entered in the record that denotes the determined time.

Figure 5A:
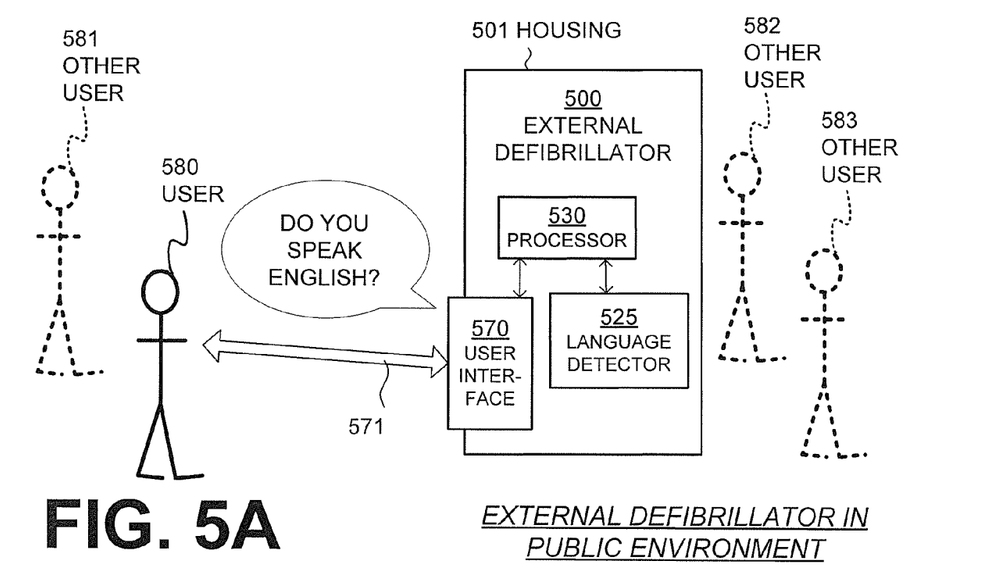
FIG. 5A is a diagram showing an external defibrillator prompting a user to provide an indication of the vicinity language according to embodiments.

FIG. 5A is a diagram showing an external defibrillator 500 prompting a user 580 to provide an indication of the vicinity language according to embodiments. Defibrillator 500 includes a housing 501, a processor 530, a language detector 525, and a user interface 570 structured to interact with, e.g., provide prompts to, the user 580 as indicated generally by 571. There may be other users 581, 582, and 583 within the vicinity of the defibrillator 500 and the user 580 as the defibrillator 500 may be situated at a public location, such as an international airport, for example. In the example, the user interface 570 is structured to prompt the user to provide an indication of the vicinity language by asking the user 580 whether he or she speaks English.

Figure 5B:
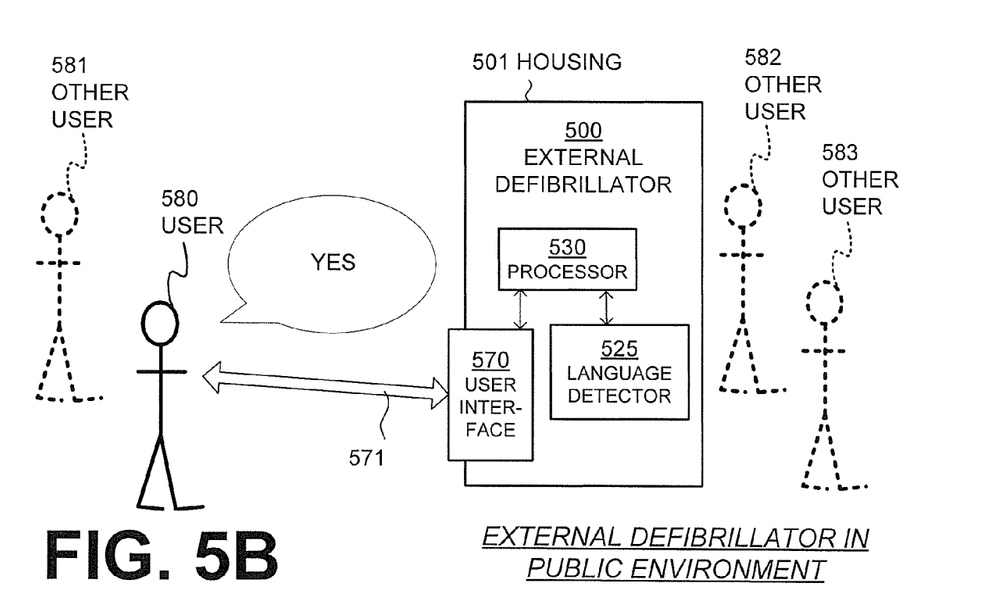
FIG. 5B is a diagram showing the user of FIG. 5A providing an indication of the vicinity language to the external defibrillator according to embodiments.

FIG. 5B is a diagram showing the user 580 of FIG. 5A providing an indication of the vicinity language to the external defibrillator 500 according to embodiments. In the example, the user 580 provides a verbal indication that the vicinity language may be English. Alternatively or in addition, the user 580 may provide the indication by way of touching a screen, button, or other component of the user interface 570.

Figure 5C:
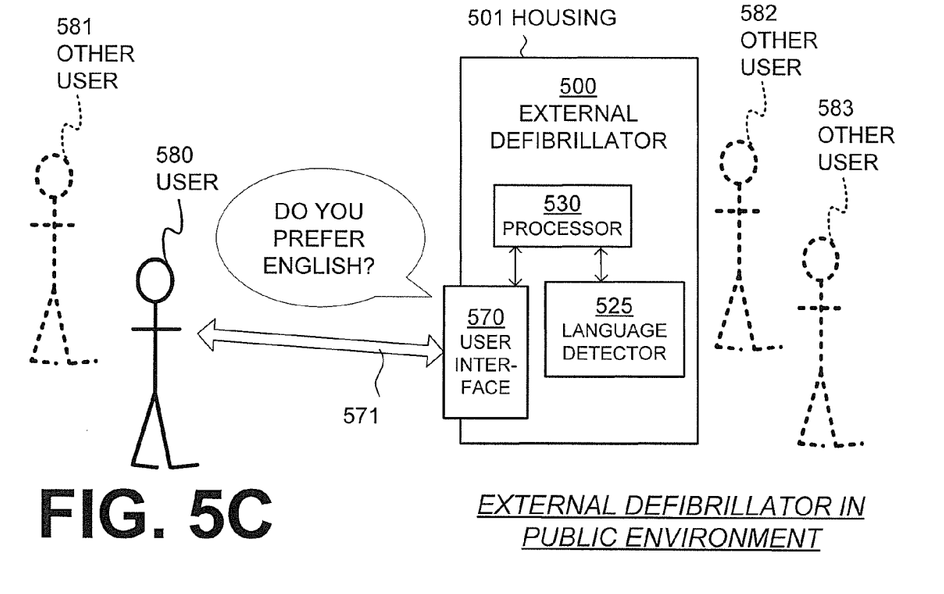
FIG. 5C is a diagram showing the external defibrillator of FIG. 5B prompting the user to provide a confirmation of the determined vicinity language according to embodiments.

FIG. 5C is a diagram showing the external defibrillator 500 of FIG. 5B prompting the user 580 to provide a confirmation of the determined vicinity language according to embodiments. For example, while the user 580 has indicated in FIG. 5B that he or she speaks English, the language may not be the user's primary language. In such situations, the vicinity language may be a different language.

Figure 5D:
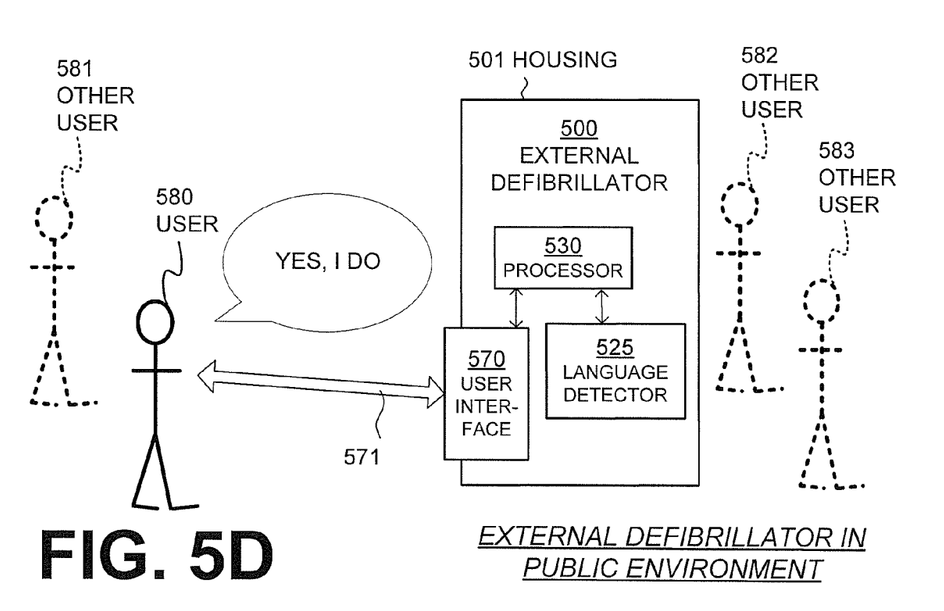
FIG. 5D is a diagram showing the user of FIG. 5C providing a confirmation of the vicinity language to the external defibrillator according to embodiments.

FIG. 5D is a diagram showing the user 580 of FIG. 5C providing a confirmation of the vicinity language to the external defibrillator 500 according to embodiments. In the example, the user 580 provides confirmation that English may be the vicinity language by verbally answering in the affirmative. Alternatively or in addition, the user 580 may provide the indication by way of touching a screen, button, or other component of the user interface 570.

Figure 6A:
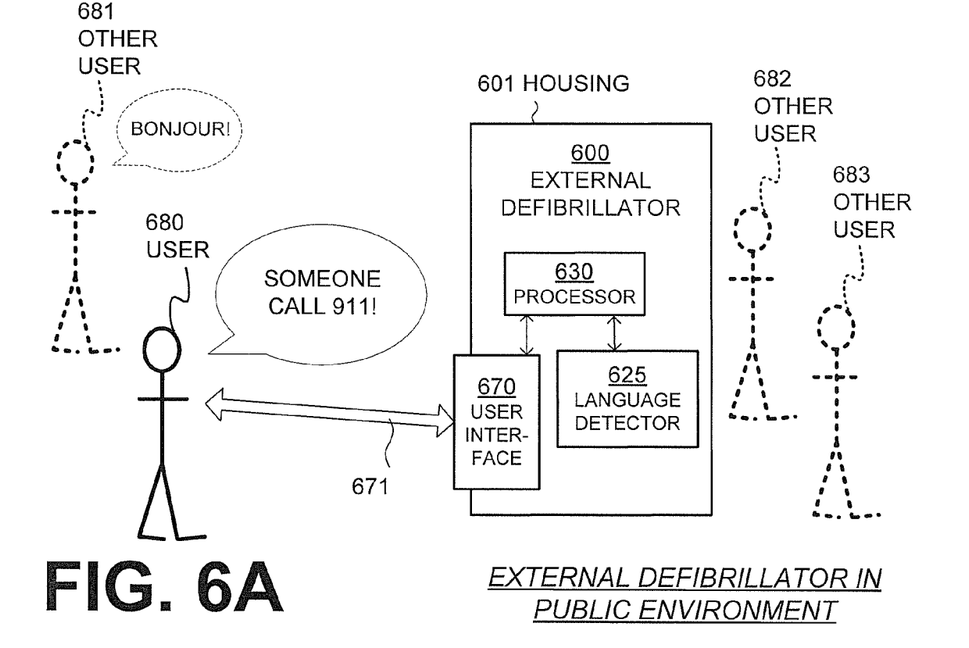
FIG. 6A is a diagram showing a user crying out for help in the vicinity of an external defibrillator according to embodiments.

FIG. 6A is a diagram showing a user 680 crying out for help in the vicinity of an external defibrillator 600 according to embodiments. Defibrillator 600 includes a housing 601, a processor 630, a language detector 625, and a user interface 670 structured to interact with, e.g., provide prompts to, the user 680, as indicated generally by 671. There may be other users 681, 682, and 683 within the vicinity of the defibrillator 600 and the user 680. For example, the defibrillator 600 may be situated at a public location, such as an international airport, where the user 680 speaks one language and at least one of the other users 681 speaks a different language.

Figure 6B:
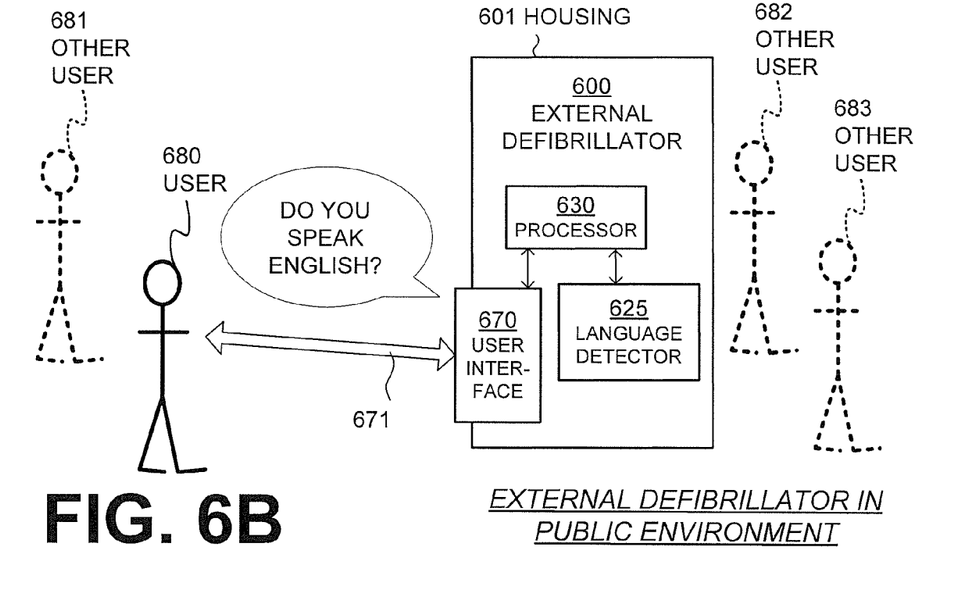
FIG. 6B is a diagram showing the external defibrillator of FIG. 6A prompting the user to provide a confirmation of the determined vicinity language according to embodiments.

FIG. 6B is a diagram showing the external defibrillator 600 of FIG. 6A prompting the user 680 to provide a confirmation of the determined vicinity language according to embodiments. In the example, the language detector 625 has made a determination that the vicinity language is English based on the user 680, who is situated closest to the defibrillator 600, crying out for help in English. Defibrillator 600 thus prompts the user 680 for confirmation of the determination by asking whether the user 680 speaks English.

Figure 6C:
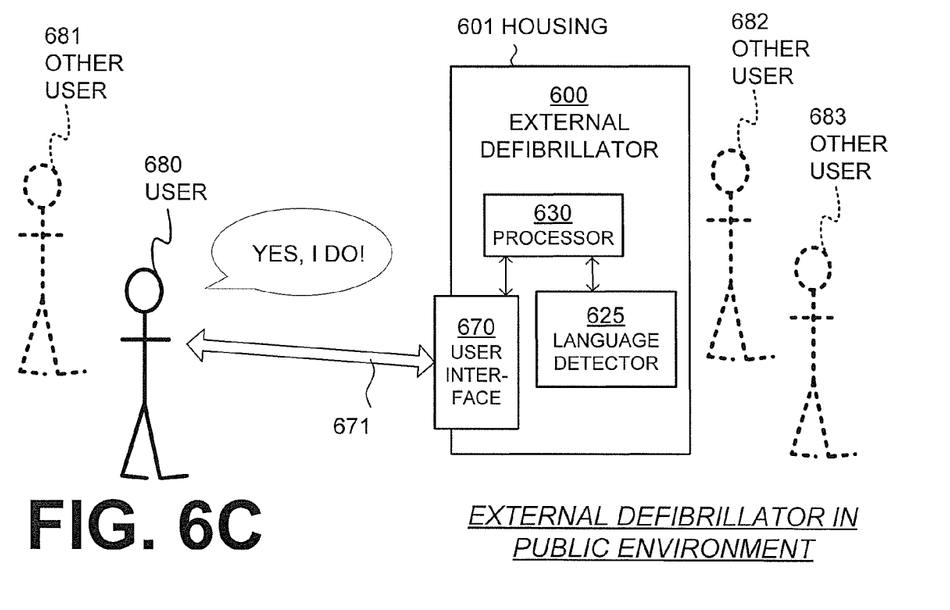
FIG. 6C is a diagram showing the user of FIG. 6B providing a confirmation of the vicinity language to the external defibrillator according to embodiments.

FIG. 6C is a diagram showing the user 680 of FIG. 6B providing a confirmation of the vicinity language to the external defibrillator 600 according to embodiments. The user 680 does so by answering the question in the affirmative, thus indicating that English is the vicinity language in the example.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 7:
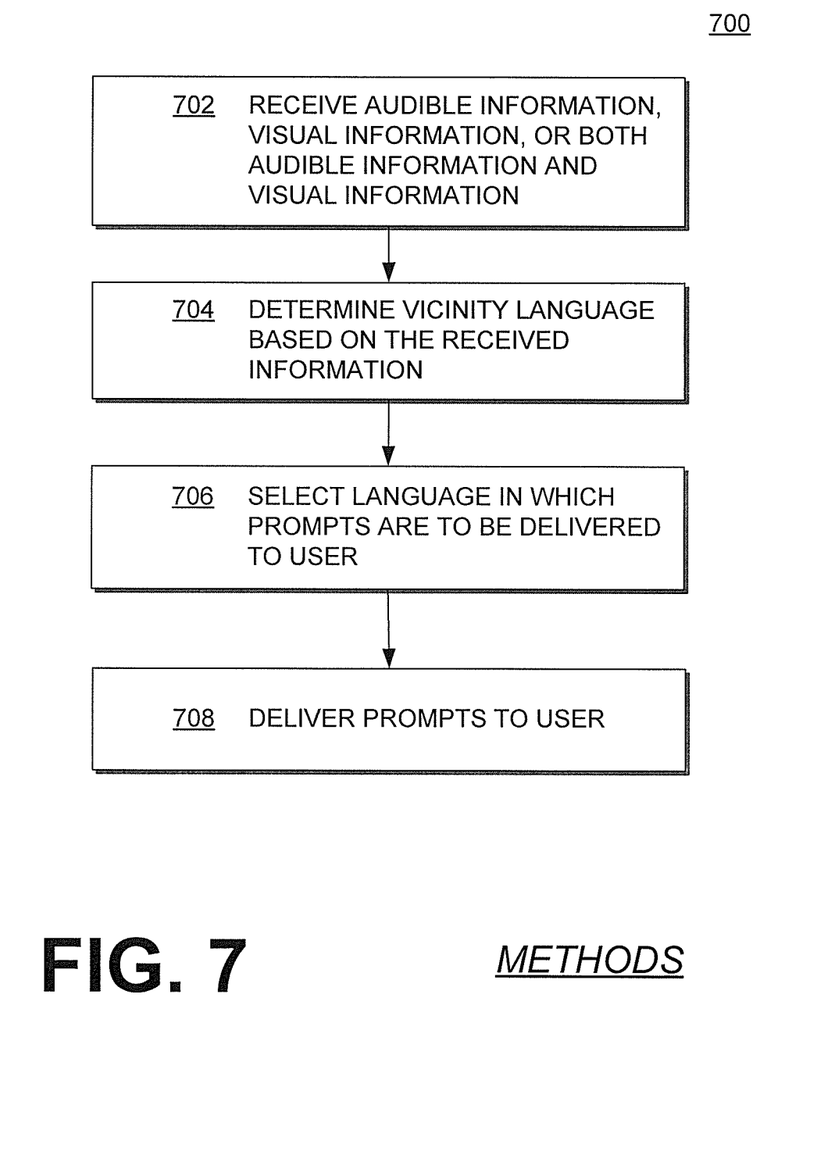
FIG. 7 is a flowchart for illustrating methods of an external defibrillator selecting a language for delivering prompts to a user according to embodiments.

FIG. 7 is a flowchart 700 for illustrating methods of an external defibrillator selecting a language for delivering prompts to a user according to embodiments.

According to an operation at 702, an external defibrillator receives vicinity information including audible information, visual information, or both audible information and visual information.

According to an operation at 704, the defibrillator determines a vicinity language based on the received vicinity information.

According to an operation at 706, the defibrillator selects a language based on the determined vicinity language. The selected language may be the determined vicinity language. Alternatively or in addition thereto, the selected language may be an initial language or a default language.

According to an operation at 708, the defibrillator delivers by way of a user interface one or more prompts to a user during a defibrillation session. The delivered prompts are in the language that is selected based on the determined vicinity language. The prompts may include audible prompts, visual prompts, or both audible prompts and visual prompts.

Figure 8:
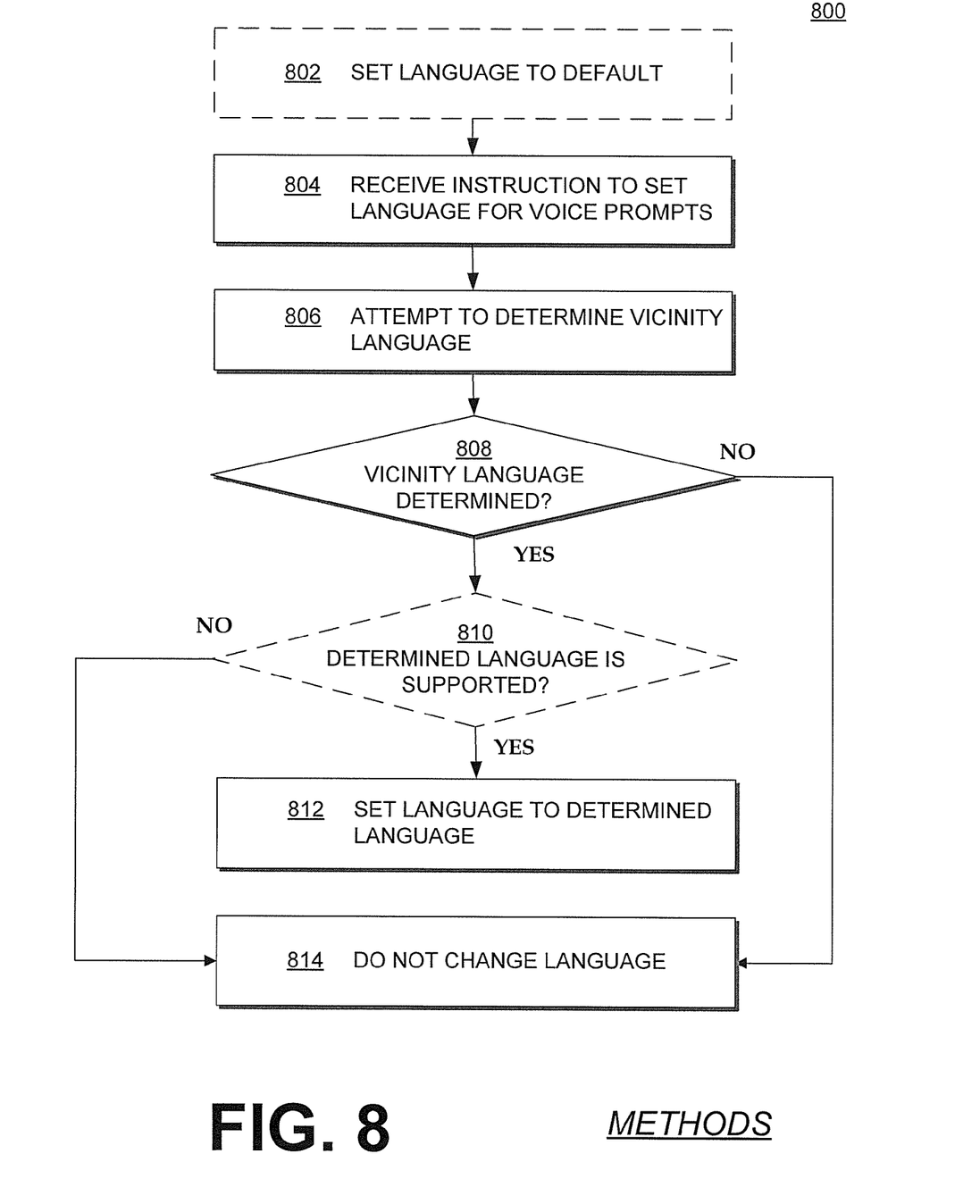
FIG. 8 is a flowchart for illustrating other methods of an external defibrillator selecting a language for delivering prompts to a user according to embodiments.

FIG. 8 is a flowchart 800 for illustrating other methods of an external defibrillator selecting a language for delivering prompts to a user according to embodiments.

According to an optional operation at 802, a default language is set. The user interface of an external defibrillator may deliver voice prompts to a user during a defibrillation session, where the voice prompts are in the default language.

According to an operation at 804, the defibrillator receives an instruction to set the language in which the voice prompts are to be delivered. The language may be the same as the default language or a different language.

According to an operation at 806, the defibrillator attempts to determine a vicinity language. For example, the defibrillator may have a language detector that is structured to determine the vicinity language based on an indication provided by a user.

According to an operation at 808, a determination is made as to whether the vicinity language has been determined. If so, processing may continue to an optional operation at 810 or directly to an operation at 812; otherwise, processing continues to an operation at 814.

According to the optional operation at 810, a determination is made as to whether the determined language is supported. For example, the defibrillator may have a language selector that is structured to determine whether the selected language is one of plurality of supported languages stored in a database. The database may be within the housing of the defibrillator or at a location that is remote from the device. Upon completion of the operation at 810, processing may continue to the operation at 812.

According to the operation at 812, the defibrillator sets the language in which the voice prompts are to be delivered to the determined language resulting from the operation at 806.

According to the operation at 814, the defibrillator does not change the language in which the voice prompts are to be delivered.

Figure 9:
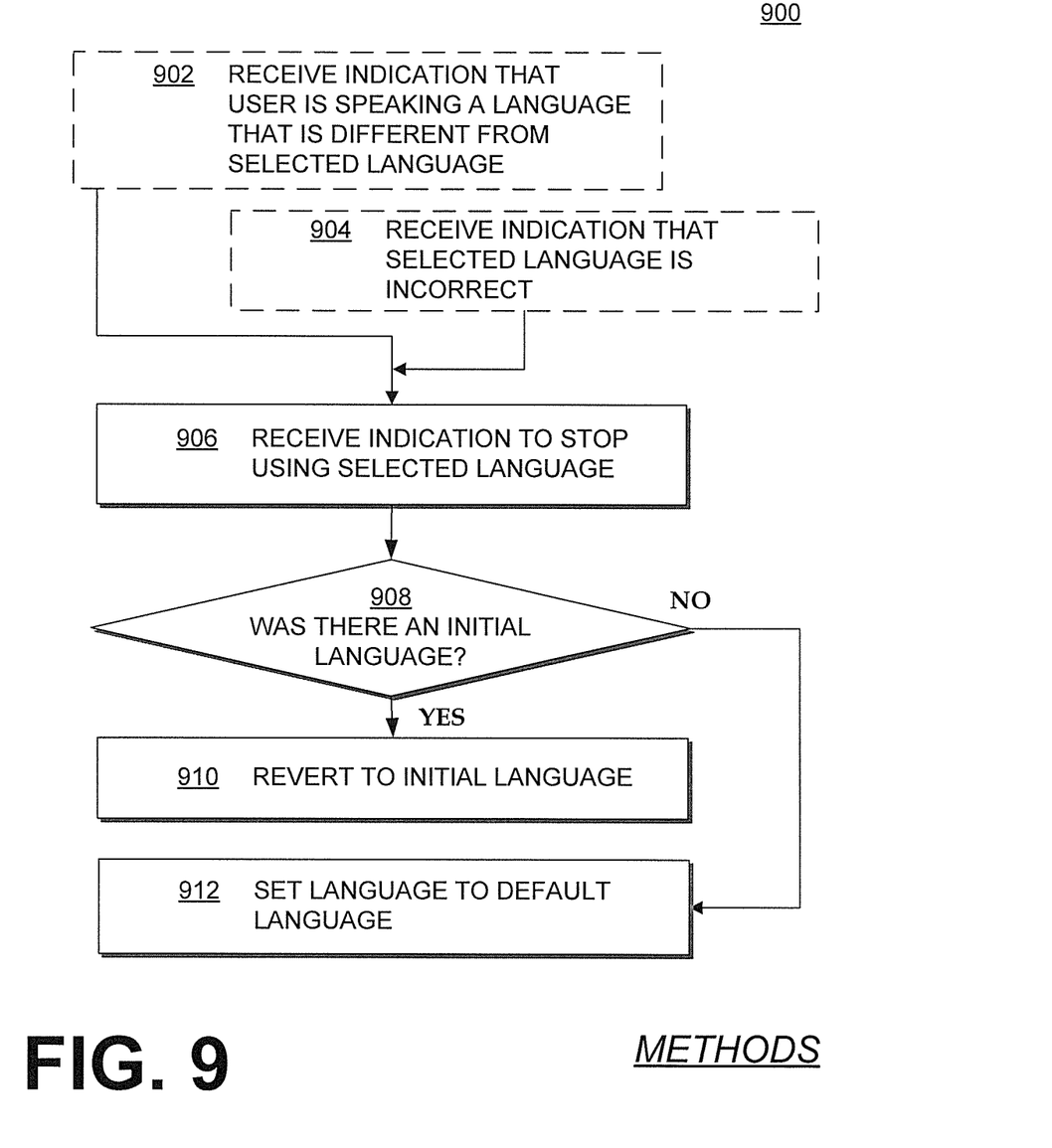
FIG. 9 is a flowchart for illustrating methods of an external defibrillator no longer using a selected language for delivering prompts to a user according to embodiments.

FIG. 9 is a flowchart 900 for illustrating methods of an external defibrillator no longer using a selected language for delivering prompts to a user according to embodiments.

According to an optional operation at 902, the defibrillator receives an indication that the user is speaking a language that is different from the language in which prompts are to be delivered to the user by a user interface during a defibrillation session.

According to an optional operation at 904, the defibrillator receives an indication that the language in which prompts are to be delivered to the user by the user interface during the defibrillation session is incorrect. For example, selection of the language may be erroneous in situations where the correct language is similar to or a dialect of at least one other language.

According to an operation at 906, the defibrillator receives an indication to stop delivering prompts to a user in the selected language, e.g., vicinity language, responsive to an indication to change languages, such as in the indications received in connection with the operations at 902 and 904, for example.

According to an operation at 908, a determination is made as to whether there was an initial language. If so, processing may continue to an operation at 910; otherwise, processing continues to an operation at 912.

According to the operation at 910, the user interface of the defibrillator may revert back to delivering the prompts to the user in the initial language.

According to the operation at 912, the defibrillator sets the language in which the prompts are to be delivered to the user by the user interface during the defibrillation session to a default language. The user interface may thus begin delivering the prompts to the user in the default language.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. An external medical device, comprising:
   a housing;
   an energy storage module within the housing for storing an electrical charge;
   a defibrillation port for guiding via electrodes the stored electrical charge to a person;
   a user interface structured to deliver prompts to a user during a defibrillation session; and
   a language detector in the housing structured to determine a vicinity language,
   in which the prompts delivered by the user interface to the user during the defibrillation session are in a language that is selected based on the determined vicinity language, and further in which the language detector includes an optical character recognition (OCR) module, or both a voice recognition module and an OCR module.

2. The device of claim 1, further comprising:
   a processor, and
   in which the processor includes the language detector.

3. The device of claim 1, in which
   the prompts include one or more audible prompts, one or more visible prompts, or a combination of one or more audible prompts and one or more visible prompts.

4. The device of claim 1, in which
   the vicinity language is a language spoken by the user when using the device.

5. The device of claim 1, further comprising:
   a language selector in the housing structured to select the language in which the prompts are delivered by the user interface to the user during the defibrillation session.

6. The device of claim 5, in which
   the language selector selects the vicinity language as the language in which the prompts are delivered by the user interface to the user during the defibrillation session.

7. The device of claim 5, in which
   the language selector selects a language other than the vicinity language as the language in which the prompts are delivered by the user interface to the user during the defibrillation session.

8. The device of claim 1, in which
   the user interface is further structured to prompt the user to provide an indication of the vicinity language, and
   in which the language detector is structured to determine the vicinity language based on the indication provided by the user.

9. The device of claim 8, in which
   the indication provided by the user comprises verbal feedback, visual cues, or verbal feedback and visual cues.

10. The device of claim 1, in which
    the user interface is further structured to prompt the user to provide a confirmation of the vicinity language.

11. The device of claim 1, in which
    a record is created from one of diagnosing and treating the person, and
    a code is entered in the record that denotes the detected vicinity language.

12. The device of claim 11, in which
    a time is further determined, and
    a code is entered in the record that denotes the determined time.

13. The device of claim 1, in which
    the user interface delivers the prompts to the user in the vicinity language.

14. The device of claim 13, in which
    the user interface is further structured to stop delivering the prompts in the vicinity language responsive to an indication to change languages.

15. The device of claim 14, in which
    the indication to change languages is based on a determination that the vicinity language is incorrect.

16. The device of claim 14, in which
    the indication to change languages is based on a determination that the user is speaking a language that is different from the vicinity language.

17. The device of claim 1, in which
    the user interface is structured to not stop delivering the prompts to the user in the selected language after a specified period of time has passed during the defibrillation session.

18. The device of claim 5, in which
    the language selector is further structured to determine whether the selected language is supported by the device.

19. The device of claim 18, in which
    responsive to a determination that the selected language is not supported by the device, the user interface is structured to use an initial language when delivering the prompts to the user.

20. The device of claim 19, in which
    the initial language is a default language.

21. The device of claim 18, further comprising:
    a database structured to store the prompts in each of a plurality of supported languages, and
    in which the language selector is structured to determine whether the selected language is one of the plurality of supported languages.

22. The device of claim 21, in which
    the database is within the housing.

23. The device of claim 21, further comprising:
    a communication module within the housing to establish a wireless connection to provide access to the database, and
    in which the database is at a location that is remote from the device.

24. The device of claim 1, in which
    the user interface is structured to present two or more language options to the user, and
    in which the two or more language options are similar to each other.

25. The device of claim 1, in which
    the language detector is structured to monitor ambient sounds.

26. The device of claim 25, in which the ambient sounds include a radio station broadcast.

27. The device of claim 25, in which the ambient sounds include a public announcement (PA) from a PA system.

28. The device of claim 1, in which the language detector is structured to select the language in which the prompts are delivered by the user interface to the user during the defibrillation session.

* * * * *